United States Patent
Richter

(10) Patent No.: US 6,430,436 B1
(45) Date of Patent: *Aug. 6, 2002

(54) TWO ELECTRODE HEART RATE MONITOR MEASURING POWER SPECTRUM FOR USE ON ROAD BIKES

(75) Inventor: Edward Richter, St. Louis, MO (US)

(73) Assignee: Digital Concepts of Missouri, Inc., Earth City, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 09/653,376

(22) Filed: Sep. 1, 2000

Related U.S. Application Data

(63) Continuation-in-part of application No. 09/260,160, filed on Mar. 3, 1999, now Pat. No. 6,115,629.

(51) Int. Cl.⁷ .............................................. A61B 5/024
(52) U.S. Cl. ..................................................... 600/520
(58) Field of Search ............................... 600/519, 520

(56) References Cited

U.S. PATENT DOCUMENTS

| | | | |
|---|---|---|---|
| 3,395,698 A | 8/1968 | Morehouse | 128/2.05 |
| 3,518,985 A | 7/1970 | Quinton | 128/2.06 |
| 3,702,113 A | 11/1972 | Blockley | 128/2.06 E |
| 3,744,480 A | 7/1973 | Gause et al. | 128/2.05 R |

(List continued on next page.)

OTHER PUBLICATIONS

Ruha, A. "A Real–Time Microprocessor QRS Detector System with a 1–ms Timing Accuracy for the Measurement of Ambulatory HRV," IEEE Transactions on Biomedical Engineering, vol. 44, No. 3, Mar. 1997, pp. 159–167.

The Applications Engineering Staff of Analog Devices, DSP Division, "Digital Signal Processing Applications Using the ADSP–2100 Family," vol. 1, pp. 458–459, 461.

Kurpis, "The New IEEE Standard Dictionary of Electrical and Electronics Terms," IEEE Std. 100–1992, p. 274.

*Primary Examiner*—Scott M. Getzow
(74) *Attorney, Agent, or Firm*—Senniger, Powers, Leavitt & Roedel

(57) ABSTRACT

A heart rate monitor for use with road bikes and other exercise equipment to calculate the user's heart rate while exercising. The monitor includes only two, first and second, electrodes and a signal processor mounted on the handle bars in a position that contacts the user when the bike is in normal use. The first electrode is disposed at a first location on the handle bars for contacting the user and for sensing the user's heart rate. The first electrode produces a first sensed signal representative of the user's heart rate. The second electrode is disposed at a second location on the handle bars for contacting the user and for sensing the user's heart rate. The second electrode produces a second sensed signal representative of the user's heart rate. The signal processor produces a difference signal indicative of a difference between the first and second sensed signals. The signal processor further includes a power spectrum analyzer calculating the user's heart rate by measuring the power spectrum of the difference signal and producing a processed heart rate signal as a function of the measured power spectrum whereby the processed heart rate signal is indicative of the heart rate of the user as sensed by the first and second electrodes. A battery pack powers the signal processor, the battery pack adapted to be mounted on the road bike or other exercise equipment. A method of monitoring the heart rate of a person is also included.

15 Claims, 10 Drawing Sheets

U.S. PATENT DOCUMENTS

| | | | | |
|---|---|---|---|---|
| 3,802,698 | A | 4/1974 | Burian et al. | 272/57 R |
| 3,938,507 | A | 2/1976 | Sarnoff et al. | 128/2.06 B |
| 4,083,366 | A | 4/1978 | Gombrich et al. | 128/2.05 T |
| 4,112,928 | A | 9/1978 | Putsch | 128/2.05 R |
| D254,569 | S | 3/1980 | Moffat et al. | D24/17 |
| 4,221,223 | A | 9/1980 | Linden | 128/706 |
| 4,223,683 | A | 9/1980 | Lown et al. | 128/706 |
| 4,244,021 | A | 1/1981 | Chiles, III | 364/413 |
| 4,278,095 | A | 7/1981 | Lapeyre | 128/689 |
| 4,319,581 | A | 3/1982 | Cutter | 128/707 |
| 4,378,111 | A | 3/1983 | Tsuchida et al. | 272/73 |
| 4,436,097 | A | 3/1984 | Cunningham | 128/707 |
| 4,790,528 | A | 12/1988 | Nakao et al. | 272/73 |
| 4,898,182 | A | 2/1990 | Hawkins et al. | 128/707 |
| 4,934,692 | A | 6/1990 | Owens | 272/73 |
| 4,938,228 | A | 7/1990 | Righter et al. | 128/690 |
| 4,938,475 | A | 7/1990 | Sargeant et al. | 272/73 |
| 5,158,093 | A | 10/1992 | Shvartz et al. | 128/707 |
| 5,191,891 | A | 3/1993 | Righter | 128/710 |
| 5,226,425 | A | 7/1993 | Righter | 128/710 |
| 5,243,993 | A | 9/1993 | Alexander et al. | 128/707 |
| 5,323,784 | A | 6/1994 | Shu | 128/707 |
| 5,337,753 | A | 8/1994 | Lekhtman | 128/706 |
| RE34,728 | E | 9/1994 | Hall-Tipping | 364/413.04 |
| 5,365,935 | A | 11/1994 | Righter et al. | 128/710 |
| 5,375,607 | A | 12/1994 | Sasagawa | 128/707 |
| 5,383,826 | A | 1/1995 | Michael | 482/3 |
| 5,394,879 | A | 3/1995 | Gorman | 128/707 |
| 5,435,315 | A | 7/1995 | McPhee et al. | 128/670 |
| 5,456,262 | A | 10/1995 | Birnbaum | 128/707 |
| 5,458,548 | A | 10/1995 | Crossing et al. | 482/6 |
| 5,462,504 | A | 10/1995 | Trulaske et al. | 482/7 |
| 5,527,239 | A | 6/1996 | Abbondanza | 482/8 |
| 5,581,369 | A | 12/1996 | Righter et al. | 358/442 |
| 5,611,346 | A | 3/1997 | Heikkilä et al. | 128/696 |
| 5,622,180 | A | 4/1997 | Tammi et al. | 128/706 |
| 5,632,279 | A | 5/1997 | Heikkilä | 128/696 |
| 5,690,119 | A | 11/1997 | Rytky et al. | 128/706 |

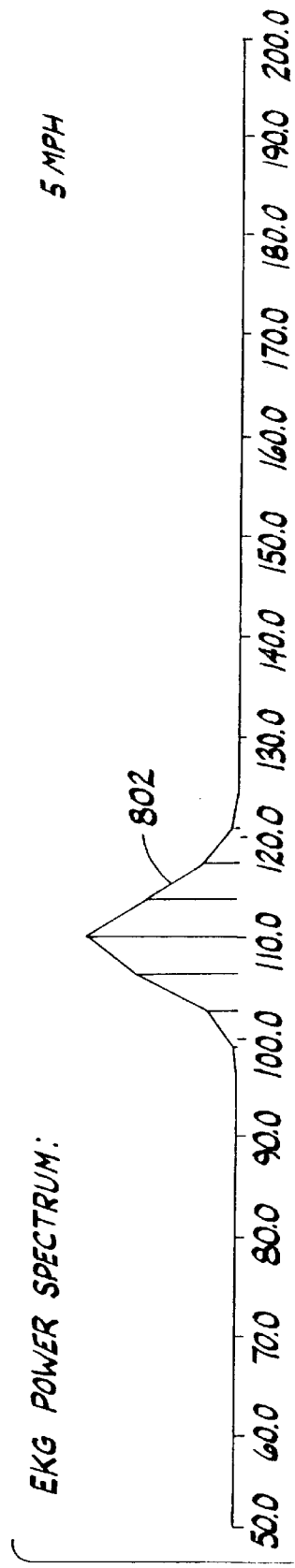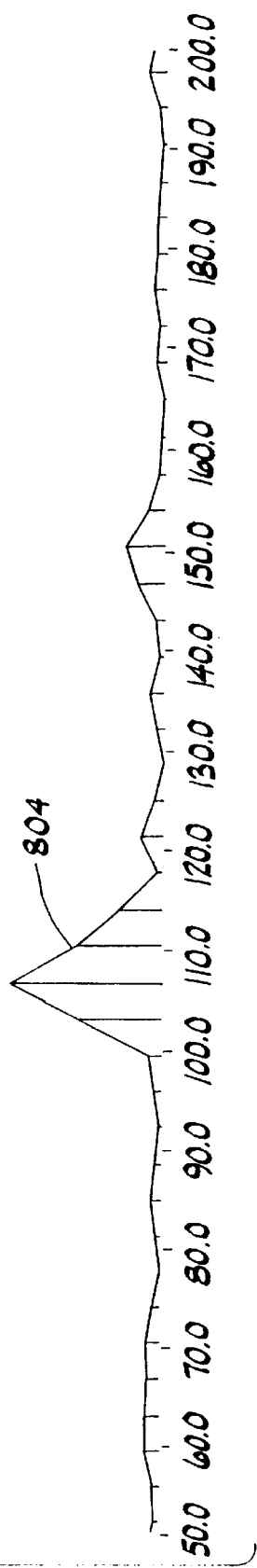
FIG. 8

TWO ELECTRODE HEART RATE MONITOR MEASURING POWER SPECTRUM FOR USE ON ROAD BIKES

CROSS-REFERENCE TO RELATED APPLICATION

This application is a continuation-in-part of U.S. Ser. No. 09/260,160, filed Mar. 3, 1999 which will issue on Sep. 5, 2000 as U.S. Pat. No. 6,115,629.

BACKGROUND OF THE INVENTION

1. Field of the Invention

The invention generally relates to heart rate monitors for use in association with exercising equipment. In particular, the invention relates to a two electrode monitor employing digital signal processing of signals detected by the electrodes.

2. Description of the Prior Art

Heart rate monitors for use with road bikes and other exercise equipment are known in the art. In general, such monitors tend to require four electrodes, two for each hand, in-order to accurately detect a beat to beat heart rate. Some patented prior art monitors include the following. U.S. Pat. No. 3,702,113 illustrates a heart rate monitor with only one electrode per hand. U.S. Pat. No. 5,243,993 discloses a heart rate monitor which includes a digital signal processor 44 for implementing autocorrelator 26, signal processor 28 and arbitrator 30. Similarly, Antii Ruha, Sami Sallinen & Seppo Nissilä, in A Real-Time Microprocessor ORS Detector System with a 1-ms Timing Accuracy for the Measurement of Ambulatory HRV, IEEE Transactions on Biomedical Engineering, March 1997, teach the use of digital signal processing in connection with monitoring a patient's heart rate.

U.S. Pat. No. 5,337,753 is directed to a four-electrode (two electrodes per hand) heart rate monitor. Specifically, it calls for a first live electrode and a first common electrode mounted on one half of an elongate member in spaced relationship with each other and a second live electrode and a second common electrode mounted on the other half of the elongate member in spaced relationship with each other.

Referring next to U.S. Pat. No. 5,337,753, it discloses an apparatus for measuring heart rate having at least the following features: (i) sensor means for generating an input signal including the biopotential signal produced by the user's heart, (ii) autocorrelating means responsive to the input signal for periodically generating an autocorrelation signal of the input signal over a predetermined time period and, (iii) signal indication means responsive to the autocorrelation signal for detecting the presence of at least one periodic signal in the autocorrelation signal and generating a heart rate signal corresponding to the detected signal (s).

U.S. Pat. No. 4,319,581 describes an apparatus having a first hand grip for attachment to one end of the handlebar of a bicycle or stationary exercise device, a second hand grip including a second means for electrically contacting the other end of said handlebar, third and fourth means disposed upon said second hand grip in spaced apart relationship and adapted to electrically engage said other hand of said user, and signal monitoring means for measuring electric pulses created in the body and for indicating the heart pulse rate of such body.

There is a need for a low cost, accurate monitor which digitally processes signals on a power spectrum basis rather than a peak to peak basis, which employs only two electrodes and which includes an isolation barrier.

SUMMARY OF THE INVENTION

It is therefore an object of this invention to provide a low cost heart rate monitor which employs only two electrodes.

It is a further object of this invention to provide an accurate heart rate monitor which may be used in combination with road bikes and other exercise equipment.

It is also an object of this invention to provide a heart rate monitor which through digital signal processing based on the power spectrum provides heart rate information which is reliable.

The invention meets these needs and objects in at least three ways. First, the invention provides only one electrode per hand which avoids the problem of sweat accumulation between electrodes. Second, the invention uses an isolation barrier which allows the monitor to meet Underwriter Laboratories' and other safety specifications. Third, the invention uses digital signal processing to calculate the power spectrum, namely the application of discrete Fourier transforms with Goertzel's algorithm, to substantially reduces noise from motion artifacts, especially when the user is exercising rigorously, so that an accurate beat rate can be detected.

In one form, the invention-comprises a heart rate monitor for use with road bikes and other exercise equipment to calculate the user's heart rate while exercising. The monitor includes first and second electrodes and a signal processor. The first electrode is disposed at a first location on the road bikes and other exercise equipment for contacting the user and for sensing the user's heart rate. The first electrode produces a first sensed signal representative of the user's heart rate. The second electrode is disposed at a second location on the road bikes and other exercise equipment for contacting the user and for sensing the user's heart rate. The second electrode produces a second sensed signal representative of the user's heart rate. The signal processor produces a difference signal indicative of a difference between the first and second sensed signals. The signal processor further includes a power spectrum analyzer calculating the user's heart rate by measuring the power spectrum of the difference signal and producing a processed heart rate signal as a function of the measured power spectrum whereby the processed heart rate signal is indicative of the heart rate of the user as sensed by the first and second electrodes.

In another form, the invention comprises a heart rate monitor for use with road bikes and other exercise equipment to calculate the user's heart rate while exercising having only two electrodes and a signal processor.

In another form, the invention comprises an exercise apparatus comprising an exercise device for exercising the user and a heart rate monitor such as noted above for use with road bikes and other exercise equipment to calculate the user's heart rate while exercising.

The invention also includes a method of monitoring the heart rate of a person comprising the steps of:

contacting the person with a first electrode for sensing the person's heart rate, the first electrode producing a first sensed signal representative of the person's heart rate;

contacting the person with a second electrode for sensing the person's heart rate, the second electrode producing a second sensed signal representative of the person's heart rate;

producing a difference signal indicative of a difference between the first and second sensed signals;

measuring the power spectrum of the difference signal; and producing a processed heart rate signal as a function of the measured power spectrum whereby the processed heart rate signal is indicative of the heart rate of the person as sensed by the first and second electrodes.

Other objects and features will be in part apparent and in part pointed out hereinafter.

BRIEF DESCRIPTION OF THE DRAWINGS

FIG. 2B illustrates the inputs and outputs of the digital signal processor-of the invention.

FIG. 8 is a graph comparing the power spectrum of the ECG signal and the adaptive heart beat peak signal of FIG. 7.

Corresponding reference characters indicate corresponding parts throughout the drawings.

DETAILED DESCRIPTION OF THE PREFERRED EMBODIMENTS

Figure 1A:
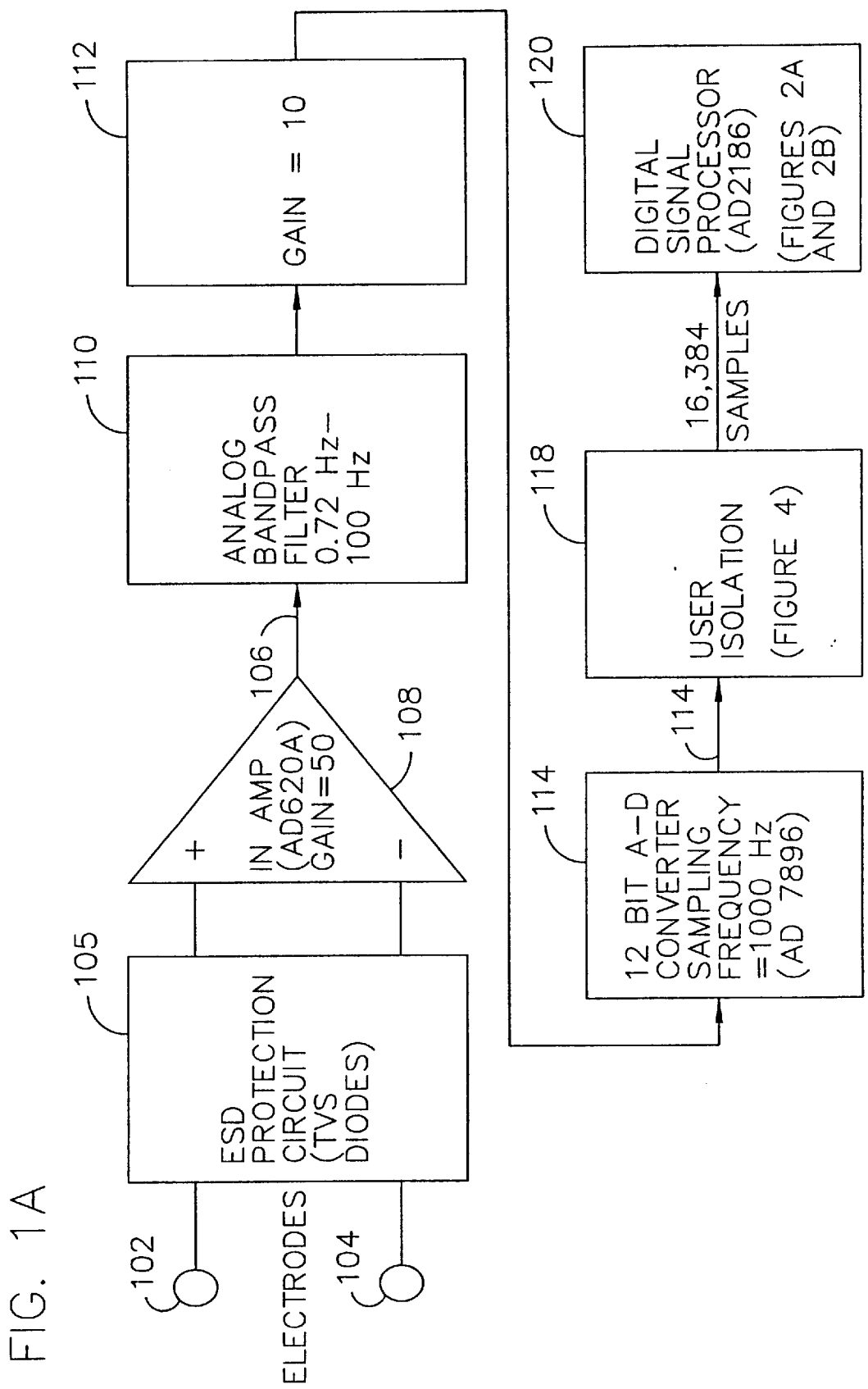
FIG. 1A is a block diagram and FIGS. 1B and 2B are schematic diagrams of one preferred embodiment of the hardware of the heart rate monitor according to the invention.
Figure 1B:
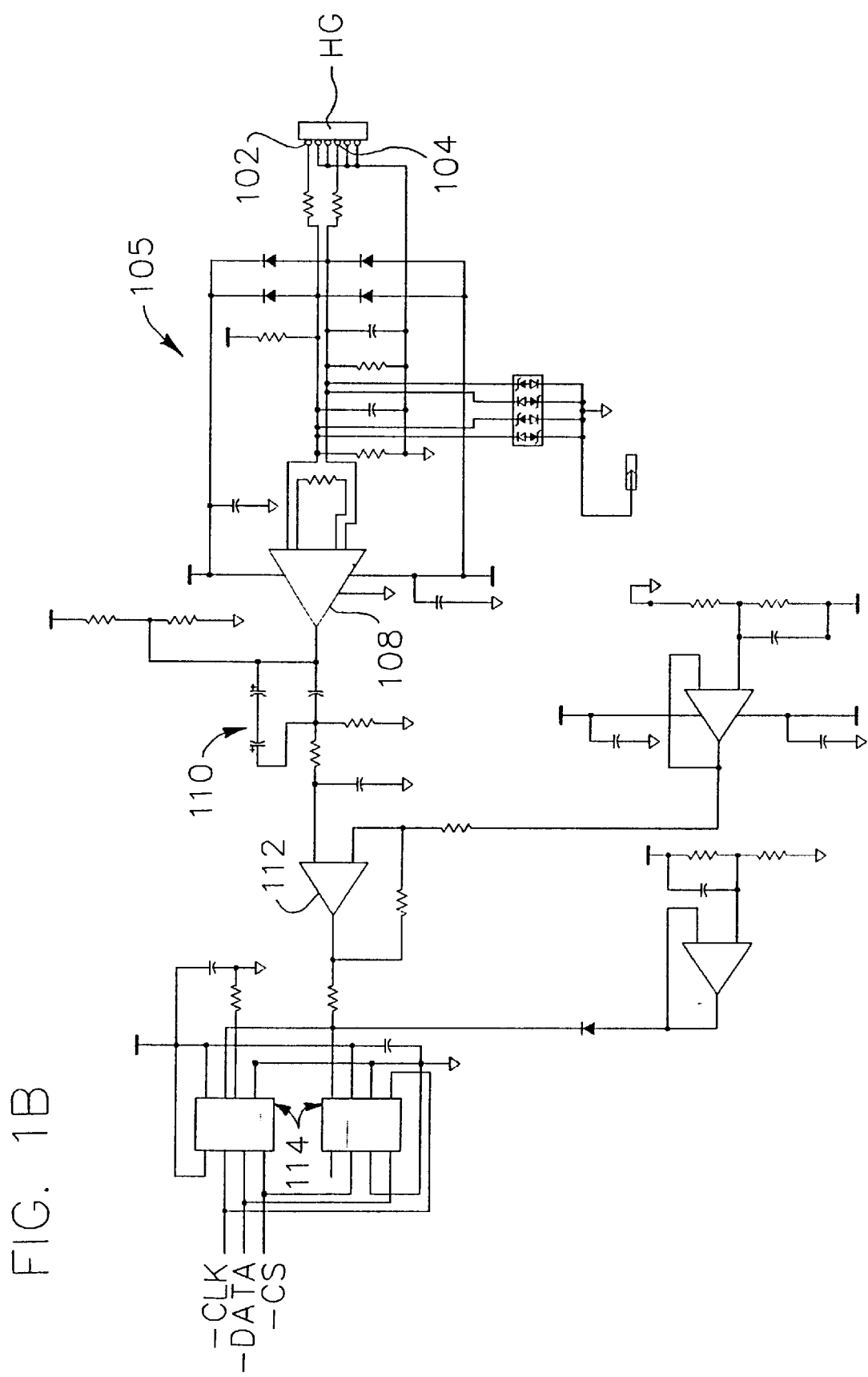
Figure 2A:
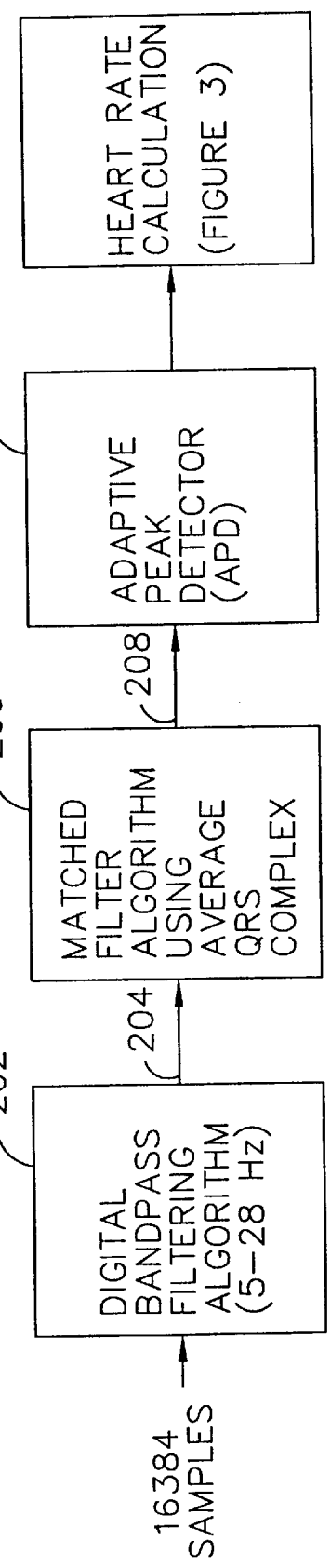
FIG. 2A illustrates in block diagram form the process employed by the digital signal processor according to the invention for generating adaptive heart beat peaks from the digital difference signal.
Figure 2C:
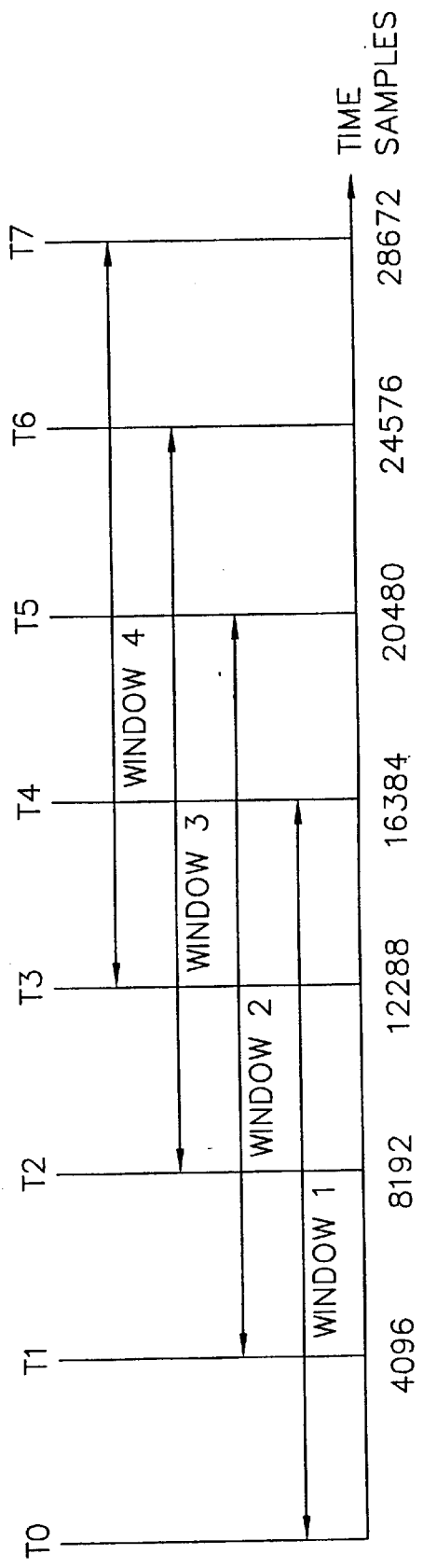
FIG. 2C illustrates the overlapping windows of successive samples which are used by the matched filter software of the digital signal processor of the invention to calculate the heart beat signal indicative of the heart rate.
Figure 2B:
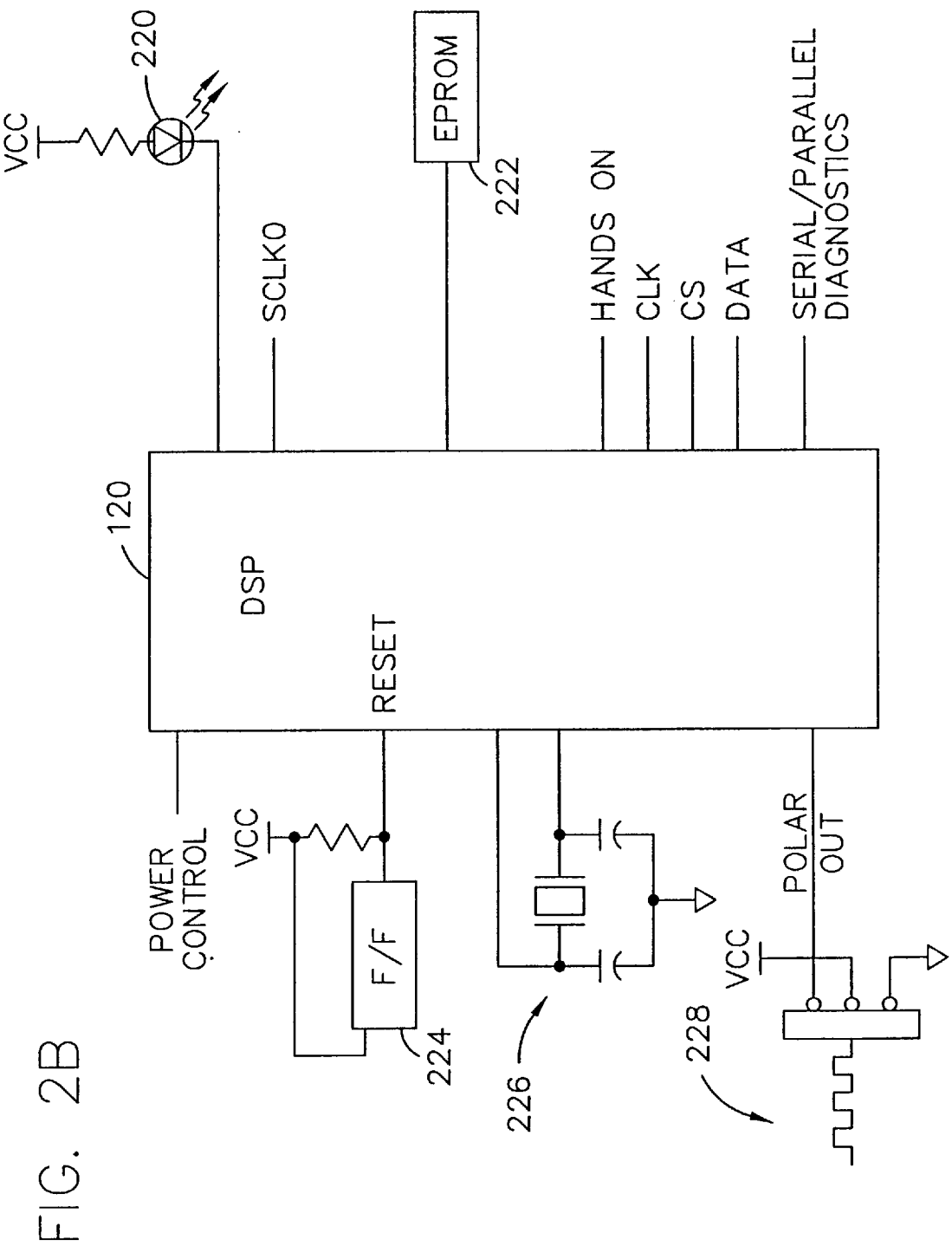

FIG. 1A is a block diagram and FIGS. 1B and 2B are schematic diagrams of one preferred embodiment of the hardware of the heart rate monitor according to the invention. In general, the heart rate monitor is contemplated for use in combination with road bikes and other exercise equipment to calculate the user's heart rate while exercising. For example, the exercise device which may be used in combination with the monitor may be a device selected from the group consisting of a treadmill, a bicycle, a skiing machine, and a step machine. In each of these devices, a handle is provided. The handle is adapted to be grasped by the user's hands. A first electrode 102 and a second electrode 104 are provided on the handle for contacting the user's hands. In general, the first electrode 102 may be disposed at any location on the road bikes and other exercise equipment as long as it is capable of being in contact with the user. Similarly, the second electrode 104 is also disposed at any location on the road bikes and other exercise equipment so that it can contact the user. Each of the electrodes senses the user's heart rate. The first electrode 102 produces a first sensed signal representative of the user's heart rate. The second electrode 104 produces a second sensed signal representative of the user's heart rate.

The electrodes. are connected through an electrostatic discharge (ESD) protection circuit to a differential amplifier 108. The equipment illustrated in block diagram form in FIG. 1A after the ESD protection circuit 105 comprises a signal processor 105 for converting the analog signals detected by the electrodes into a digital heart rate. Initially, differential amplifier 108 produces a difference signal via line 106. The difference signal 106 is indicative of a difference between the first and second sensed signals provided by the electrodes 102 and 104.

The difference signal 106 is then passed through a bandpass filter 110 such as an analog filter which only allows signals having a frequency of at least 0.72 Hz and a frequency not more than 100 Hz to pass to an amplifier 112 which amplifies the signal. Preferably, amplifier 112 would have a gain of 10. The amplified signal is then provided to a 12 bit analog to digital converter having a 1,000 Hz sampling frequency. For example, this converter 114 may be an AD7896 manufactured by Analog Devices. The converter provides a digital difference signal 116 to an isolating circuit 118 which provides electrical isolation between the user and the power source. The output of the converter 114 includes 1,000 samples per second which are provided through the isolation circuit 118 to a digital processor 120. For example, processor 120 may be an ADSP-2186 as manufactured by Analog Devices. In general, the converter 114 may be a sampling circuit or sampling software for converting the analog difference signal 106 after it has been filtered by bandpass filter 110 and amplified by amplifier 112 into a corresponding digital difference signal 116.

As shown in FIG. 1B, a hand grip connector HG provides the connection to the electrodes 102 and 104 which are provided to the differential amplifier 108 and converted to digital DATA signals. Accompanying the DATA signals are a clock signal CLK providing a timing reference for the digital data and a chip select CS providing a hand shake protocol.

FIG. 2A illustrates the process employed by the digital signal processor 120 according to the invention for generating adaptive heart beat peaks from the digital difference signal 116 provided as 1,000 samples per second to the digital signal processor 120 via the isolating circuit 118. As will be described below in greater detail regarding FIG. 2B, the digital signal processor 120 comprises a microprocessor. In one aspect of the invention, the microprocessor employs software (stored in EPROM 222, FIG. 2B) which executes a digital signal processing algorithm including a digital band pass filtering algorithm 202 which passes signals in the range of 5–28 Hz to provide a filtered digital difference signal via line 204. Such signals correspond to the bandwidth of the QRS complex. Next, as illustrated by block 206, the processor 120 employs a matched filter algorithm to provide a heart beats signal via line 208 from the filtered digital difference signal provided via line 204. In general, the matched filter is applied to the average QRS complex of successive, overlapping windows of the filtered digital difference signal in order to detect the heart beats, eliminate noise and generate a digital signal representative thereof.

In one aspect of the invention, the digital processor employs overlapping windows as illustrated in FIG. 2C to evaluate the waveform being provided by the series of samples.

In particular, referring to FIG. 2C, assume that the converter 114 begins sampling at time T0 so that at time T1, 4,096 samples have been provided to the processor 120. These samples are considered to be the first part of window 1. The 4,096 samples between times T1 and T2 are the first part of window 2 and the second part of window 1. Similarly, the 4,096 samples between times T2 and T3 are considered to be the first part of window 3, the second part of window 2, and third part of window 1. Finally, the 4,096 samples between times T3 and T4 is considered to be the first part of window 4, the second part of window 3, the third part of window 2, and the last part of window 1. At time T4, window 1 is considered to be a completed waveform and at time T5 window 2 is completed so that these windows can now be compared to each other according to matched filtering by processor 120. As illustrated in FIG. 2C, window 2 overlaps window 1 by 75%. Essentially, window 2 drops the first 4,096 samples provided during time T0 to T0 and adds the 4,096 samples provided between time T4 and T5. Subsequent windows 3 and 4 are similarly defined based on the previous windows. Therefore, by comparing successive windows to each other, noise is minimized or eliminated and a waveform representative of the heart beats results after the matched filter comparison.

Next, the digital signal processor 120 employs software which functions as an adaptive peak detector 210 so that the digital signal provided via line 212 is converted into heart beats peaks.

FIG. 2B illustrates the inputs and output of the digital signal processor 120. Operation of the digital signal processor 120 provides a POWER CONTROL signal and a start clock (reset) signal SCLKO to control the dc/dc power supply (see FIG. 4) and a voltage source VCC which also illuminates a light emitting diode to visually indicate that power has been applied to the digital signal processor 120. In addition, processor 120 loads its instructions from an EPROM 222 which is programmed with the various algorithms and functions as noted herein along with any other applications needed to operate the monitor. A microprocessor supervisor circuit 224 resets the processor whenever the voltage VCC drops below a minimum. An oscillator 226 provides a reference clock signal to the processor 120. In addition, the processor 120 generates the clock signal CLK, a chip select signal CS and receives the DATA signal as processed from the electrodes.

Optionally, the processor may have serial and/or parallel ports for debugging and diagnostics. After processing, the processor 120 provides a POLAR OUT signal in the form of a square wave 228 having a period frequency corresponding the calculated heart rate. This POLAR OUT signal is a standard format which interfaces with most road bikes and other exercise equipment and is the same formatted signal transmitted by wireless heart rate detectors. Optionally, if the road bikes and other exercise equipment accommodates wireless detectors transmitting rf signals, the processor can be programmed so that such rf signals override the signals being detected by the electrodes.

Figure 3:
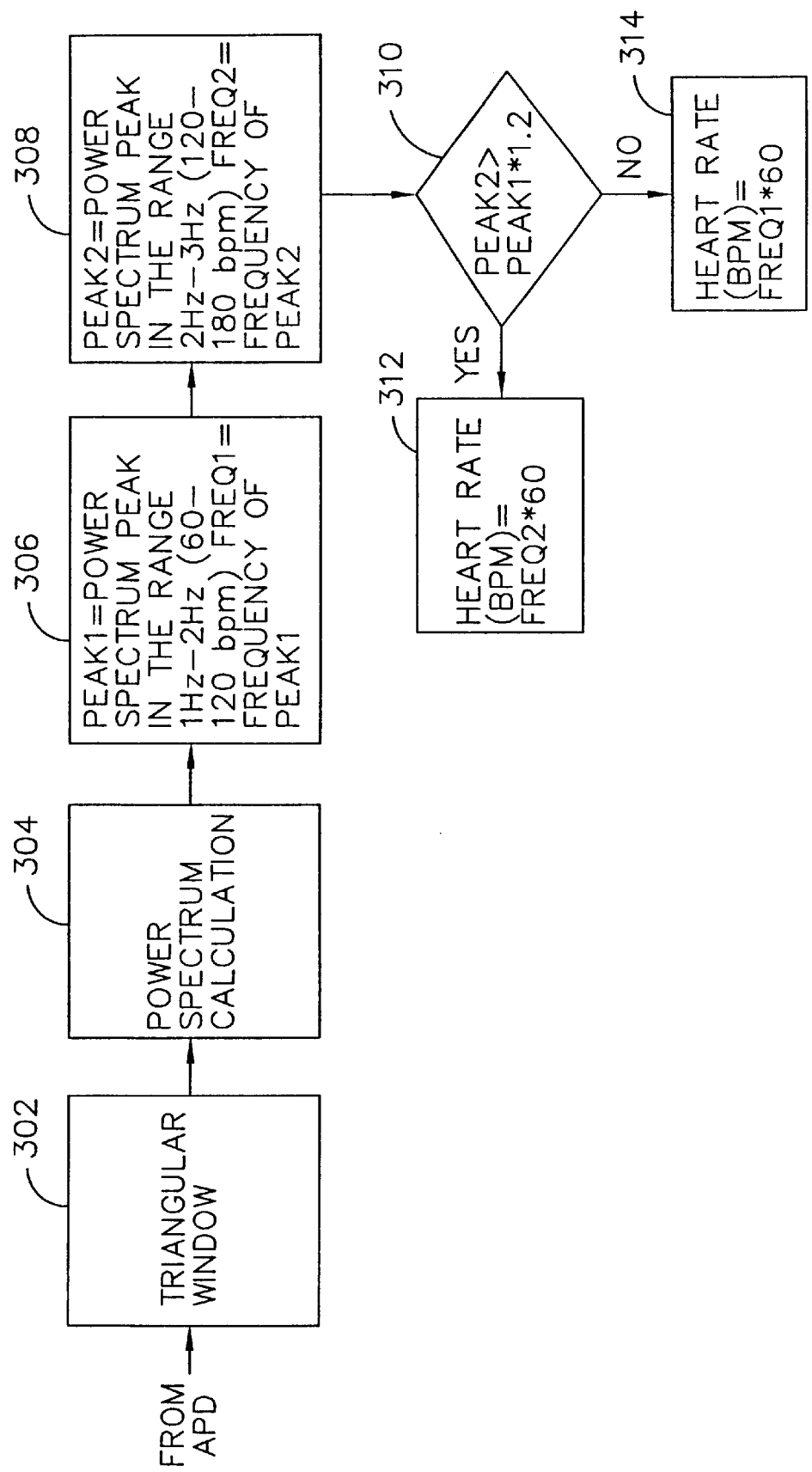
FIG. 3 illustrates the process employed by the digital signal processor according to the invention to generate a heart rate calculation from the adaptive heart beat peaks.

Now that the heart beats peaks have been established by the processor 120, the heart rate calculation can be executed as illustrated in FIG. 3. Initially, as shown in FIG. 3, the heart beat peaks are processed through a triangular window 302 and then provided to software which evaluates the heart beat peaks to determine a power spectrum calculation 304. The power spectrum is calculated using Goertel's algorithm, but there are other ways to calculate it. Windowing can be done many different ways. Although the preferred embodiment used triangular, many other windowing functions would work. This yields a processed heart rate signal which will have a power spectrum peak in the range of 1–2 Hz if the beats per second are in the range of 60–120 bpm. Alternatively, the processed heart rate signal may have a power spectrum peak in the range of 2–3 Hz when the heart rate is in the range of 120–180 bpm.

The digital signal processor 120 at step 310 compares peak 2 to peak 1 multiplied by a factor of 1.2. If the processed heart rate signal has a peak 2 which is greater than peak 1 times 1.2, the processor 120 proceeds to step 312 to define the heart rate as the frequency rate of peak 2 times 60. On the other hand, if peak 2 is equal to less than peak 1 times 1.2, the processor 120 proceeds to step 314 to define the heart rate as equal to the frequency 1 of peak 1 times 60.

Figure 4:
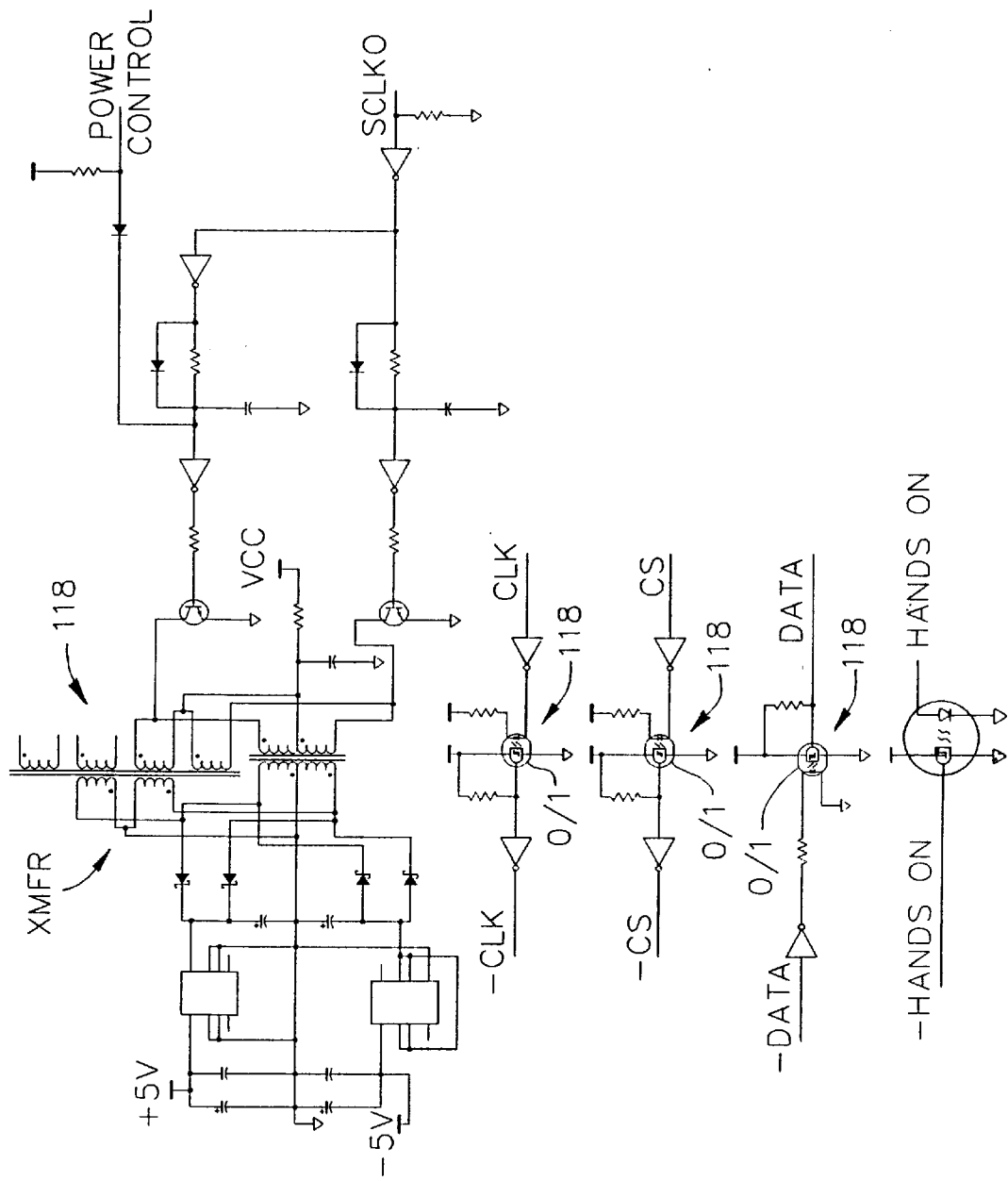
FIG. 4 is a schematic diagram of the isolation barriers according to the invention.

One aspect of the invention is that the above configuration allows for electrical isolation between the electrodes and the road bikes and other exercise equipment as shown in FIG. 4. In particular, a transformer XFMR provides isolation between the +/−5 volt power signals and the right side of FIG. 4 including the user engaging the hand grip HG, and the VCC source signal, the POWER CONTROL signal and the start clock (reset) SCLKO signal generated by the digital signal processor 120. In addition, optisolators I/O provide isolation between the clock signal CLK, chip select signal CS and DATA signal on one side of the optoisolators and their complementary signals on the other side of the optoisolators, where the user is positioned and engaged.

Figure 5:
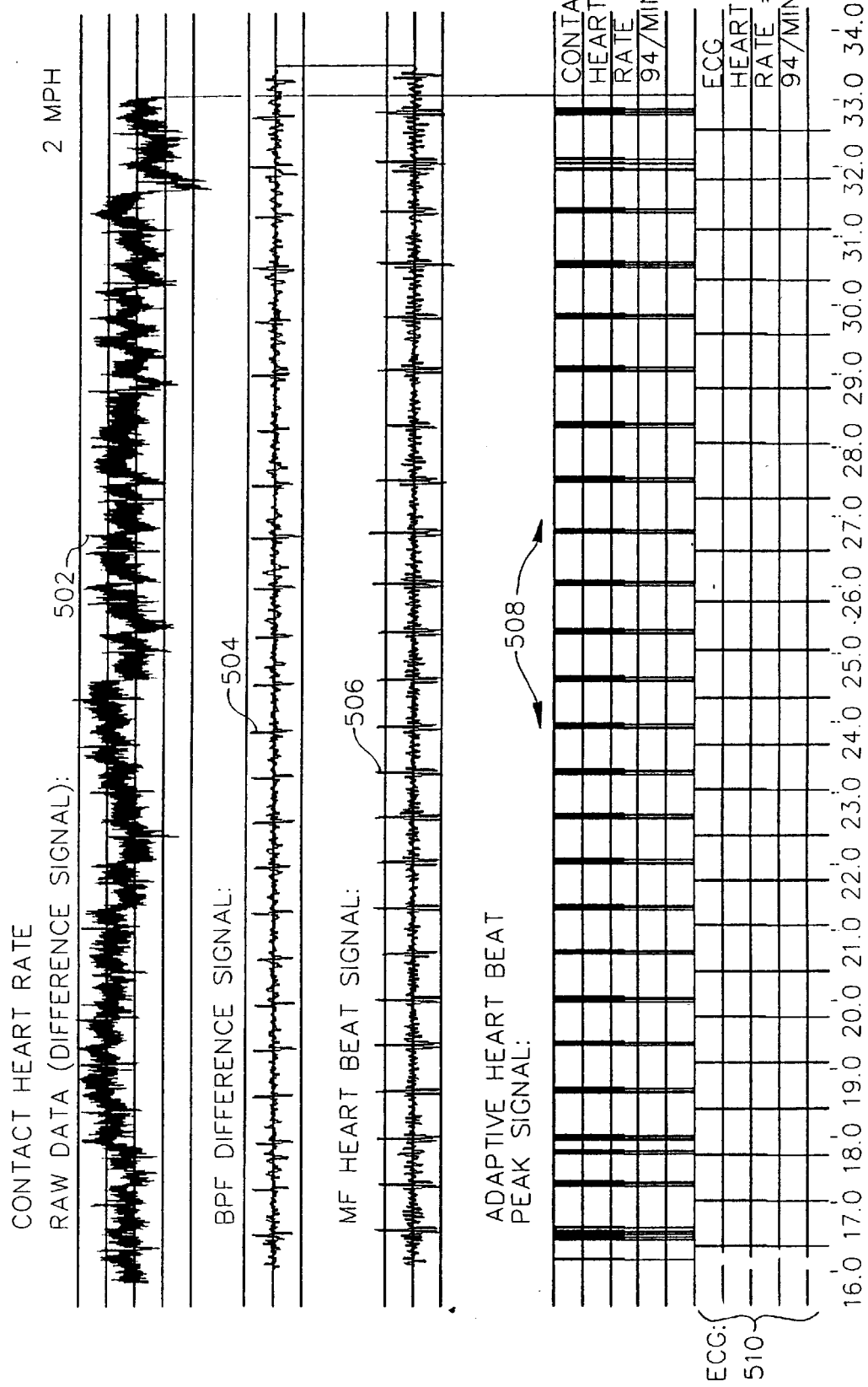
FIG. 5 is a graph which illustrates the difference signal which is the raw data from the electrodes generated by a person exercising at 2 mph and which further illustrates the following signals corresponding thereto: the analog bandpass filtered (BPF) difference signal, the matched filter (MF) heart beat signal, the adaptive heart beat peak signal and the heart rate signal measured by an ECG monitor (Polar).
Figure 6:
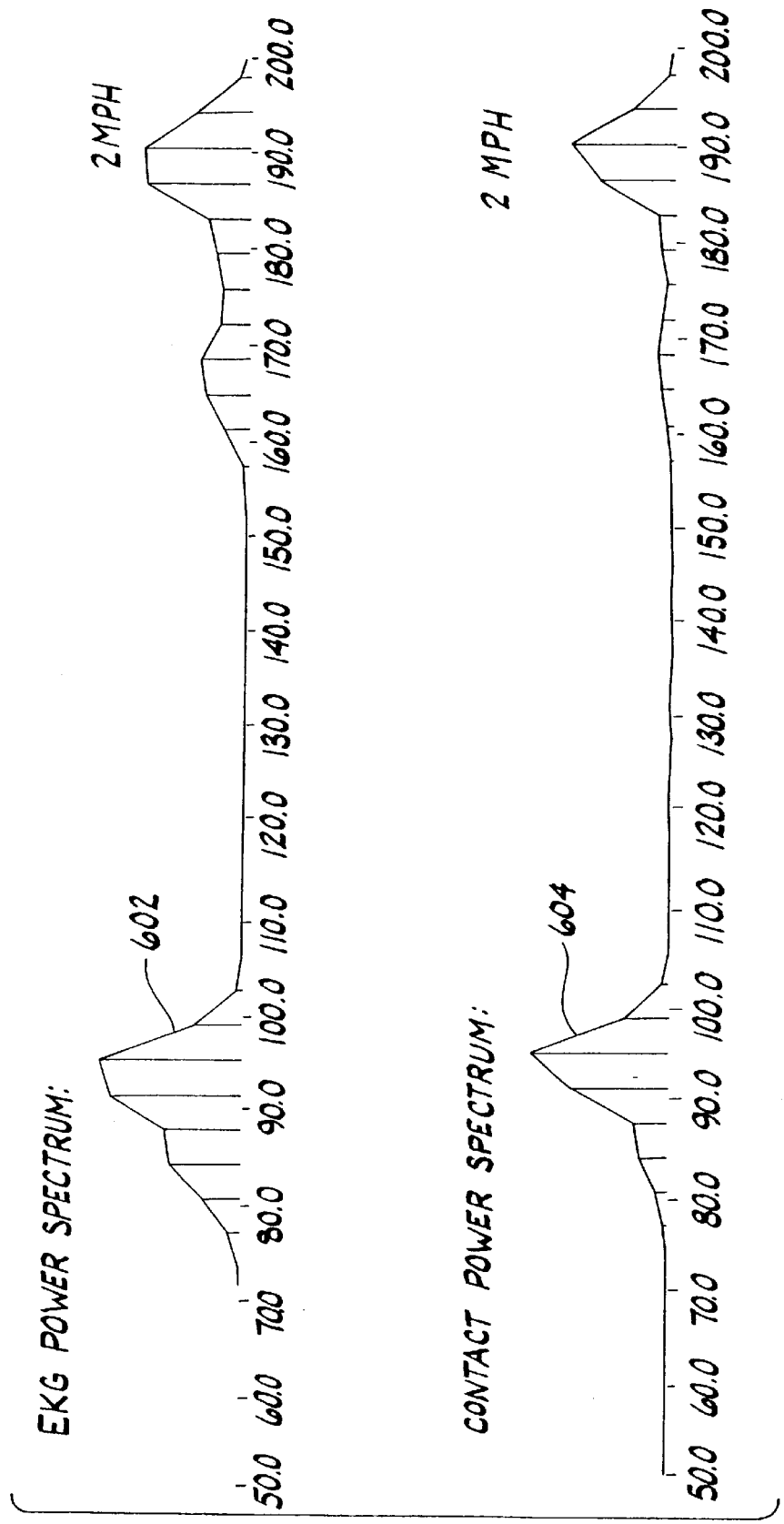
FIG. 6 is a graph comparing the power spectrum of the ECG signal and the adaptive heart beat peak signal of FIG. 5.

FIG. 5 is a graph illustrating the various waveforms which are processed beginning with the analog signals provided by the electrodes 102 and 104 to the processed digital heart rate signals which define the heart rate. Waveform 502 illustrates the raw data in the form of the analog difference signal being provided via line 106. Waveform 504 illustrates the analog difference signal after processing by bandpass filter 110. Waveform 506 illustrates the analog heart beat signal after it has been processed by the matched filter software 206 and is represented by line 208. Waveform 508 is a digital signal and represents the digital heart beat signal after it has been processed by adaptive peak detector 210. This signal defines the heart beat peaks which are processed from the power spectrum as illustrated by FIG. 3 to make the heart rate calculation. By comparison, ECG waveform 510 is derived from an electrocardiogram (ECG) of the heart being monitored by the invention. A comparison of waveforms 508 and 510 indicates that the calculated heart rate of 94 bpm as illustrated by waveform 508 is the same as the actual heart rate of 94 bpm as detected and illustrated by the ECG waveform 510. The waveforms of FIG. 5 are representative of an individual exercising at a rate of 2 mph on a treadmill and are based on actual monitored data. FIG. 6 further compares the detected ECG power spectrum 602 to the calculated power spectrum of the detected adaptive heart beat peaks signal 604. FIG. 6 illustrates a close coordination between the detected and monitored power spectrums.

Figure 7:
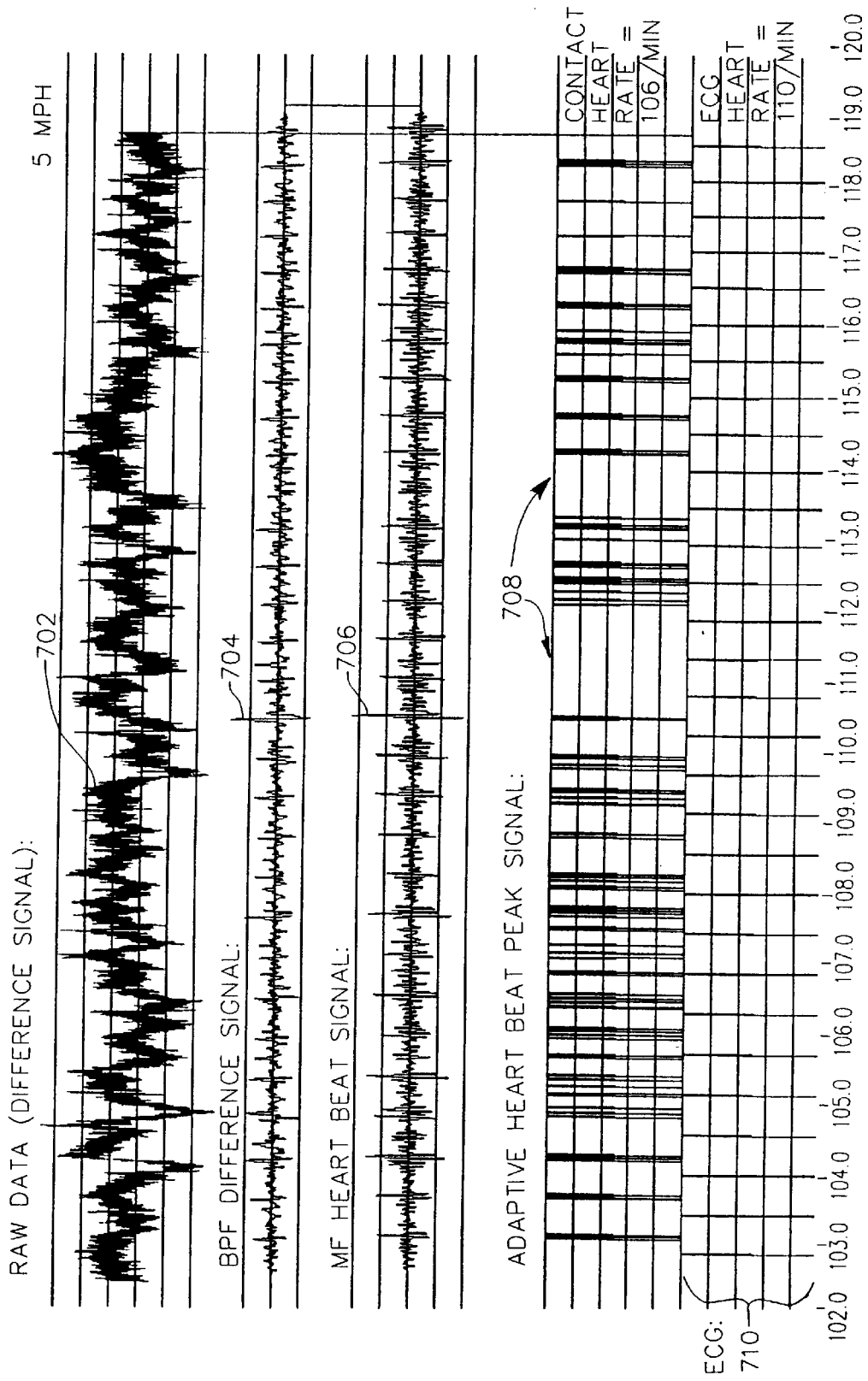
FIG. 7 is a graph which illustrates the difference signal which is the raw data from the electrodes generated by a person exercising at 5 mph and which further illustrates the following signals corresponding thereto: the analog bandpass filtered (BPF) difference signal, the matched filter (MF) heart beat signal, the adaptive heart beat peak signal and the electrocardiogram (ECG) signal.

Similarly, FIGS. 7 and 8 are representative of an individual exercising at a rate of 5 mph on a treadmill and illustrate actual monitored data. FIG. 7 is a graph illustrating the various waveforms which are processed beginning with the analog signals provided by the electrodes 102 and 104 to the processed digital heart rate signals which define the heart rate. Waveform 702 illustrates the raw data in the form of the analog difference signal being provided via line 106. Waveform 704 illustrates the analog difference signal after processing by bandpass filter 110. Waveform 706 illustrates the analog heart beat signal after it has been processed by the matched filter software 206 and is represented by line 208. Waveform 708 is a digital signal and represents the digital heart beat signal after it has been processed by adaptive peak detector 210. This signal defines the heart beat peaks which are processed from the power spectrum as illustrated by FIG. 3 to make the heart rate calculation. By comparison, ECG waveform 710 is derived from an electrocardiogram (ECG) of the heart being monitored by the invention. A comparison of waveforms 708 and 710 indicates that the calculated heart rate of 106 bpm as illustrated by waveform 708 is the very similar to the actual heart rate of 110 bpm as detected and illustrated by the ECG waveform 710. FIG. 8 further compares the detected ECG power spectrum 802 to the calculated power spectrum of the detected adaptive heart beat peaks signal 804. FIG. 8 illustrates a close coordination between the detected and monitored power spectrums.

By way of illustration only, the peak 1 and peak 2 calculations of steps 306 and 308, respectively, may be accomplished by executing the following algorithm:

$$Peak(j) = \frac{\sum PowerSpectrum(j)}{ENBW}$$

For j=i−span/2, . . . i+span/2, where i=peak index, where PowerSpectrum(j)=power in bin j, and where ENBW=equivalent noise bandwidth of the window (e.g., 1.5).

As an example of determining the peak calculation for 2 mph, the digital signal processor 120 would perform the following calculations:

$$Peak(j) = \sum_{j=i-1}^{i+1} \frac{PowerSpectrum(j)}{1.5}$$

PowerSpectrum[12]=1.21E−5

PowerSpectrum[13]=1.68E−5

PowerSpectrum[14]=5.24E−6

Peak [13]=(1.21E−5+1.68E−5+5.24E−6)/1.5

Peak [13]=2.28E−5

From the ECG waveform 510 in FIG. 5, the peak [13] reads 2.28E−5, which is the same as the peak as calculated above by the digital signal processor 120.

Similarly, by way of illustration only, the calculation of frequency 1 and frequency 2 by steps 306 and 308, respectively, may be accomplished by employing the following algorithm in the digital signal processor 120:

$$Freq(j) = \frac{\sum PowerSpectrum(j)*(j*dF)}{\sum PowerSpectrum(j)}$$

For j=i−span/2, . . . i+span/2, where i=peak index, where PowerSpectrum(j)=power in bin j, and where dF=frequency bin width.

As an example of determining the frequency calculation for 2 mph, the digital signal processor 120 would perform the following calculations:

$$Freq(j) = \frac{\sum_{j=i-1}^{i+1} PowerSpectrum(j)*(j*dF)}{\sum_{j=i-1}^{i+1} PowerSpectrum(j)} *60 + BPMoffset$$

$$dF = 1000/16384 = 6.104E-2$$

$$BPMoffset = 47.61 \text{ bpm}$$

$$Freq(13) = 60 * \frac{[(1.21E-5)(12*6.104E-2) + (1.68E-5)(13*6.104E-2) + (5.24E-6)(14*6.104E-2)]}{(1.21E-5)+(1.66E-5)+(5.24-6)} + 47.61$$

$$Freq(13) = 94.47$$

From the ECG 510 in FIG. 5, the frequency[1] reads 94.47, which is the same as the frequency as calculated above by the is digital signal processor 120.

It is particularly contemplated that the invention may be used with any display console that has a polar interface. The interface to the display console consists of three wires which mimics a polar receiver. In general, the system would operate in the following manner. The digital signal processor 120 detects when the hand grips are held and starts to search for a pulse. The signal input to the digital signal processor (i.e., the samples) are very noisy and their pulse amplitude is relatively small. Therefore, the processor uses the digital filtering algorithm 202 to define the samples. Preferably, the processor 120 records sixteen seconds of signal information that the digital band pass filtering algorithm 202 reduces to a filter digital difference signal. For this sixteen second period, the processor will not indicate a heart rate to its display console. After the sixteen second period, and after a heart rate is detected, updates are averaged every four seconds.

The sixteen seconds of initial data after the hand grips are first held are not displayed. Preferably, the processor 120 would be programmed to indicate through the display that the monitor is in the mode of searching for a pulse rate.

It is possible to display a heart rate at 8 to 12 seconds, but it is lower in resolution and less reliable.

The invention also includes a method of monitoring the heart rate of a person comprising the steps of:

contacting the person with a first electrode for sensing the person's heart rate, the first electrode producing a first sensed signal representative of the person's heart rate;

contacting the person with a second electrode for sensing the person's heart rate, the second electrode producing a second sensed signal representative of the person's heart rate;

producing a difference signal indicative of a difference between the first and second sensed signals;

measuring the power spectrum of the difference signal; and producing a processed heart rate signal as a function of the measured power spectrum whereby the processed heart rate signal is indicative of the heart rate of the person as sensed by the first and second electrodes.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

What is claimed is:

1. A heart rate monitor for use with road bikes or other exercise equipment having handle bars to calculate the user's heart rate while exercising, said monitor comprising:

a first electrode disposed at a first location on the handle bars for contacting the user and for sensing the user's heart rate, said first electrode producing a first sensed signal representative of the user's heart rate;

a second electrode disposed at a second location on the handle bars for contacting the user and for sensing the user's heart rate, said second electrode producing a second sensed signal representative of the user's heart rate;

a signal processor which produces a difference signal indicative of a difference between the first and second sensed signals, said signal processor further including a power spectrum analyzer calculating the user's heart rate by measuring the power spectrum of the difference signal and producing a processed heart rate signal as a function of the measured power spectrum whereby the processed heart rate signal is indicative of the heart rate of the user as sensed by the first and second electrodes; and a battery pack for powering the signal processor, said battery pack adapted to be mounted on the road bike or other exercise equipment.

2. The monitor of claim 1 further comprising a converter for converting the difference signal into a corresponding digital difference signal, wherein the signal processor comprises a digital signal processor and wherein the digital signal processor analyzes overlapping windows of successive samples of the digital difference signal.

3. The monitor of claim 1 further comprising a converter for converting the difference signal into a corresponding digital difference signal, wherein the signal processor comprises a digital signal processor receiving the digital difference signal and wherein the digital signal processor employs a Fourier transform analysis to provide the processed heart rate signal from the digital difference signal.

4. The monitor of claim 3 wherein the digital signal processor employs a Goertzl algorithm as part of the Fourier transform analysis.

5. The monitor of claim 1 further comprising a converter for converting the difference signal into a corresponding digital difference signal, wherein the signal processor comprises a digital signal processor receiving the digital difference signal and wherein the digital signal processor employs a matched filter algorithm to provide a heart beats signal from the digital difference signal.

6. The monitor of claim 5 wherein the digital signal processor employs an adaptive peak detector to determine heart beat peaks from the provided heart beats signal and wherein the digital signal processor employs a triangular window and a power spectrum calculation to provide the processed heart rate signal indicative of the heart rate from the determined heart beat peaks.

7. The monitor of claim 1 wherein the signal processor comprises a sampler for converting the difference signal into a corresponding digital difference signal and wherein the power spectrum analyzer comprises a digital signal processor which analyzes the digital difference signal and provides the processed heart rate signal in response thereto.

8. The monitor of claim 7 wherein the sampler comprises an analog-to-digital converter converting the difference signal into the corresponding digital difference signal and wherein the signal processor comprises a microprocessor employing a digital signal processing algorithm which executes digital bandpass filtering of the digital difference signal to provide a filtered digital difference signal.

9. The monitor of claim 7 including a isolating circuit between the sampler and the digital signal processor, said isolating circuit receiving the digital difference signal and providing an isolated digital difference signal to the digital signal processor.

10. The monitor of claim 1 wherein the signal processor comprises a differential amplifier receiving the first and second sensed signals and providing the difference signal corresponding thereto and a sampler for converting the difference signal into a corresponding digital difference signal and wherein the power spectrum analyzer comprises a digital signal processor which analyzes the digital difference signal and provides the processed heart rate signal in response thereto.

11. The monitor of claim 1 further comprising a TVS diode circuit receiving the first and second sensed signals and providing a first ESD protected signal and a second ESD protected signal corresponding thereto and wherein the difference signal is a function of the difference between the first and second ESD protected signals.

12. The monitor of claim 11 further comprising a differential amplifier receiving the first and second ESD protected signals and providing the difference signal corresponding thereto.

13. A heart rate monitor for use with road bikes or other exercise equipment having handle bars to calculate the user's heart rate while exercising, said monitor comprising:

only two electrodes comprising:

a first electrode disposed at a first location on the handle bars for contacting the user and for sensing the user's heart rate, said first electrode producing a first sensed signal representative of the user's heart rate; and a second electrode disposed at a second location on the handle bars for contacting the user and for sensing the user's heart rate, said second electrode producing a second sensed signal representative of the user's heart rate;

a signal processor receiving the first and second sensed signals and producing a difference signal indicative of a difference between the first and second sensed signals, said signal processor producing a processed heart rate signal corresponding to a power spectrum of the difference signal wherein the processed heart rate signal is indicative of the heart rate of the user as sensed by the first and second electrodes; and a battery pack for powering the signal processor, said battery pack adapted to be mounted on the road bike or other exercise equipment.

14. An exercise apparatus for exercising a user comprising:

a road bike having handle bars, said road bike for exercising the user; and a heart rate monitor for use with the road bike to calculate the user's heart rate while exercising, said monitor comprising:

a first electrode disposed at a first location on the handle bars for contacting the user and for sensing the user's heart rate, said first electrode producing a first sensed signal representative of the user's heart rate;

a second electrode disposed at a second location on the handle bars for contacting the user and for sensing the user's heart rate, said second electrode producing a second sensed signal representative of the user's heart rate;

a signal processor which produces a difference signal indicative of a difference between the first and second sensed signals, said signal processor further including a power spectrum analyzer calculating the user's heart rate by measuring the power spectrum of the difference signal and producing a processed heart rate signal as a function of the measured power spectrum whereby the processed heart rate signal is indicative of the heart rate of the user as sensed by the first and second electrodes; and a battery pack for powering the signal processor, said battery pack adapted to be mounted on the road bike or other exercise equipment.

15. The exercise apparatus of claim 14 wherein the exercise device comprises a device selected from the group consisting of a treadmill, a bicycle, a skiing machine and a step machine, wherein the device has a handle adapted to be grasped by the user's hands and wherein the electrodes are on the handle for contacting the user's hands.

* * * * *